(12) United States Patent
Dwyer et al.

(10) Patent No.: US 7,437,931 B2
(45) Date of Patent: *Oct. 21, 2008

(54) MEDICAL APPLICATION FOR NO-MOTION SENSOR

(75) Inventors: Michael D. Dwyer, Seminole, FL (US); John W. Thornberry, Largo, FL (US); David N. Girard, Tampa, FL (US)

(73) Assignee: Honeywell International Inc., Morristown, NJ (US)

( * ) Notice: Subject to any disclaimer, the term of this patent is extended or adjusted under 35 U.S.C. 154(b) by 52 days.

This patent is subject to a terminal disclaimer.

(21) Appl. No.: 11/459,545

(22) Filed: Jul. 24, 2006

(65) Prior Publication Data

US 2008/0016961 A1 Jan. 24, 2008

(51) Int. Cl.
*G01P 15/00* (2006.01)
*G01P 3/00* (2006.01)

(52) U.S. Cl. .......................... 73/495; 73/511; 702/141; 702/142

(58) Field of Classification Search .................... 73/495, 73/489, 491, 488, 510, 511; 702/141, 142, 702/149, 160, 184
See application file for complete search history.

(56) References Cited

U.S. PATENT DOCUMENTS

| 4,813,436 | A  | * | 3/1989  | Au .............................. 600/592 |
| 6,763,320 | B2 | * | 7/2004  | Kimble ....................... 702/182 |
| 6,836,744 | B1 | * | 12/2004 | Asphahani et al. .......... 702/141 |
| 7,028,546 | B2 | * | 4/2006  | Hoshal ........................ 73/489 |
| 7,028,547 | B2 | * | 4/2006  | Shiratori et al. ............... 73/495 |
| 7,035,436 | B2 | * | 4/2006  | Nakamura et al. .......... 382/107 |
| 7,204,145 | B2 | * | 4/2007  | Heinks et al. ................. 73/510 |
| 7,237,446 | B2 | * | 7/2007  | Chan et al. ................. 73/865.4 |

* cited by examiner

*Primary Examiner*—Helen C. Kwok
(74) *Attorney, Agent, or Firm*—Black Lowe & Graham PLLC (57) ABSTRACT

A sensor unit to detect a stillness event, the sensor unit including a gyroscope attached to a monitored person, a micro-controller communicatively coupled to the gyroscope, and a memory communicatively coupled to receive and to store the angular velocity data with a correlated time. The gyroscope senses an angular velocity of the monitored person and outputs angular velocity data based on the sensed angular velocity. The micro-controller receives the angular velocity data and recognizes a quiescence-pattern data in the angular velocity data.

17 Claims, 5 Drawing Sheets

MEDICAL APPLICATION FOR NO-MOTION SENSOR

CROSS-REFERENCE TO RELATED APPLICATIONS

This application is related to U.S. patent application Ser. No. 11/459,553 having a title of "MEDICAL USE ANGULAR RATE SENSOR" (also referred to here as the "H0012340.73693 Application"), which is filed on the same date herewith. The H0012340.73693 application is hereby incorporated herein by reference.

BACKGROUND

Elderly people living alone or in assisted living facilities are susceptible to medical emergencies in which they are alive but unconscious. In such a case, they often require medical assistance within a short time after falling unconscious. For example, an elderly person can have an immobilizing stroke, heart attack or go into diabetic shock or coma. In such a case they are not able to move in order to call for assistance. In many cases if help is received quickly, the immobilized person has an improved prognosis and increased rate of recovery from the immobilizing ailment. In some cases, delay of many hours is fatal to the person.

It is desirable to have a compact, lightweight low cost, accurate sensor system to provide data that is used to summon assistance in the event of an immobilizing medical problem. It is desirable for the sensor to be small and lightweight so it is comfortable for the monitored person to wear. Otherwise the monitored person is likely to take it off.

SUMMARY

One aspect of the present invention is a sensor unit to detect a stillness event, the sensor unit including a gyroscope attached to a monitored person, a micro-controller communicatively coupled to the gyroscope, and a memory communicatively coupled to receive and to store the angular velocity data with a correlated time. The gyroscope senses an angular velocity of the monitored person and outputs angular velocity data based on the sensed angular velocity. The micro-controller receives the angular velocity data and recognizes a quiescence-pattern data in the angular velocity data.

DRAWINGS

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Figure 1:
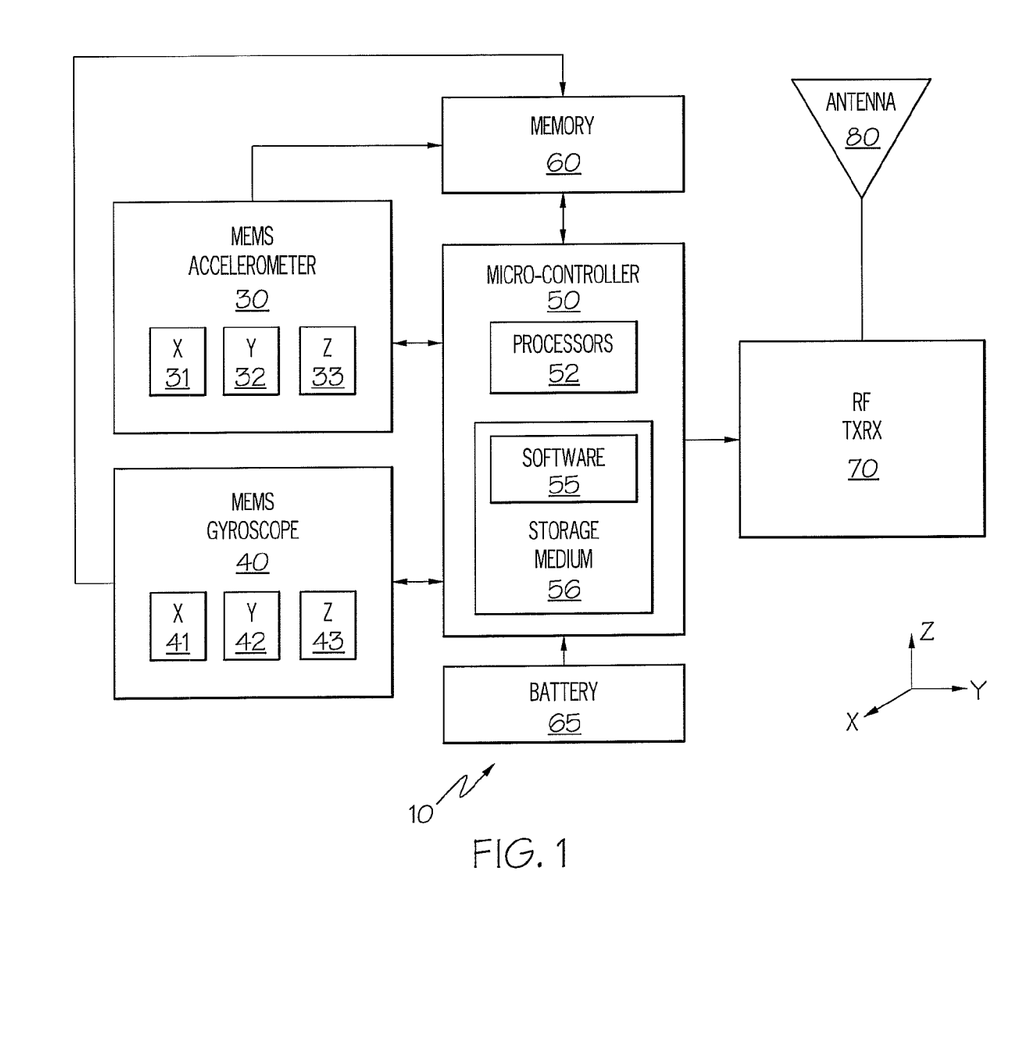
FIG. 1 is a block diagram of one embodiment of a sensor unit to detect a stillness event in accordance with the present invention.

FIG. 1 is a block diagram of one embodiment of a sensor unit 10 to detect a stillness event in accordance with the present invention. The sensor unit 10 includes a gyroscope 40, an accelerometer 30, a micro-controller 50, a memory 60, a battery 65, a transceiver 70 and an antenna 80. The gyroscope 40 is referred to here as a "micro-electro-mechanical system (MEMS) gyroscope 40" although other gyroscopes can be used in the sensor unit 10. Likewise, the accelerometer 30 is referred to here as a "micro-electro-mechanical system (MEMS) accelerometer 30" although other accelerometers can be used in the sensor unit 10. The gyroscope 40 and the accelerometer 30 measure the angular velocity and the linear acceleration, respectively, in at least two dimensions. The angular velocity is the rate of turning and is expressed in degrees/second or radians/second. The MEMS gyroscope 40 and the MEMS accelerometer 30 are small, lightweight and low cost so the sensor unit 10 is also small, lightweight and low cost. The micro-controller 50 recognizes quiescence-pattern data in the acceleration/velocity data received from the accelerometer 30 and the gyroscope 40. As defined herein, the acceleration/velocity data includes the linear acceleration sensed by the accelerometer 30 and the angular velocity sensed by the gyroscope 40. In one implementation of this embodiment, the micro-controller 50 generates an angular acceleration by differentiating the angular velocity. In this case, the acceleration/velocity data includes the linear acceleration sensed by the accelerometer 30 and the angular acceleration calculated from the angular velocity sensed by the gyroscope 40. In another implementation of this embodiment, the acceleration/velocity data includes the linear acceleration sensed by the accelerometer 30, the angular velocity sensed by the gyroscope 40, and the angular acceleration calculated from the angular velocity sensed by the gyroscope 40.

The quiescence-pattern data includes zero-value linear acceleration data and zero-value angular velocity data for a duration greater than a selected duration. In one implementation of this embodiment, the quiescence-pattern data includes zero-value linear acceleration data and zero-value angular acceleration data (calculated from the angular velocity data) for a duration greater than a selected duration.

The sensor unit 10, including the gyroscope 40, is attached to a monitored person in order to monitor the angular velocity of the monitored person. The gyroscope 40 senses an angular velocity of the monitored person and outputs angular velocity data based on the sensed angular velocity.

As shown in FIG. 1, the MEMS gyroscope 40 includes an X-direction gyroscope sensor 41 aligned for a selected X axis, a Y-direction gyroscope sensor 42 aligned for a selected Y axis, a Z-direction gyroscope sensor 43 aligned for a selected Z axis. The X-direction gyroscope sensor 41, the Y-direction gyroscope sensor 42, and the Z-direction gyroscope sensor 43 measure angular velocity about the X axis, the Y axis and the Z axis, respectively. The relative changes in the sensed acceleration/velocity data, such as the turn rate measured in degrees/second, are monitored for a stillness event. The X axis, the Y axis and the Z axis are orthogonal to each other as shown by the basis vectors X, Y, and Z in FIG. 1. In one implementation of this embodiment, there is no Z-direction gyroscope sensor 43.

The accelerometer 30 as part of the sensor unit 10 is also attached to the monitored person. The accelerometer 30 senses a linear acceleration of the monitored person and outputs linear acceleration data based on the sensed linear acceleration. In one implementation of this embodiment, the accelerometer 30 is attached to one part of the monitored person's body and the gyroscope 40 is attached to another part of the monitored person's body. In another implementation of this embodiment, the accelerometer 30 is co-located with the gyroscope 40.

As shown in FIG. 1, the MEMS accelerometer 30 includes an X-direction accelerometer sensor 31 aligned along the selected X axis, a Y-direction accelerometer sensor 32 aligned along the selected Y axis, a Z-direction accelerometer sensor 33 aligned along the selected Z axis. The X-direction accelerometer sensor 31, the Y-direction accelerometer sensor 32, and the Z-direction accelerometer sensor 33 measure linear acceleration along the X axis, the Y axis and the Z axis, respectively. In one implementation of this embodiment, relative changes in the sensed acceleration/velocity data are monitored for a stillness event.

The micro-controller 50 is communicatively coupled to the gyroscope 40 to receive the angular velocity data from the gyroscope 40. The micro-controller 50 is also communicatively coupled to the accelerometer 30 to receive the linear acceleration data from the accelerometer 30. The micro-controller 50 recognizes the quiescence-pattern data in the sensed angular velocity data and linear acceleration data. In one implementation of this embodiment, the micro-controller 50 wirelessly communicates with the gyroscope 40 and the accelerometer 30 via transceivers in the micro-controller 50, the gyroscope 40 and the accelerometer 30. The wireless communication link (for example, a radio-frequency (RF) communication link) can be a short range communication provided according to Bluetooth or WiFi standards. In another implementation of this embodiment, the micro-controller 50 communicates with the gyroscope 40 and the accelerometer 30 via wired communication link (for example, an optical fiber or copper wire communication link).

In one implementation of this embodiment, the sensor unit 10 includes an accelerometer 30 and does not include a gyroscope 40. In this case, the micro-controller 50 recognizes the quiescence-pattern data in the sensed linear acceleration data. In another implementation of this embodiment, the sensor unit 10 includes a gyroscope 40 and does not include the accelerometer 30. In one implementation of this latter embodiment, the micro-controller 50 recognizes the quiescence-pattern data in the sensed angular velocity data. In another implementation of this latter embodiment, the micro-controller 50 generates angular acceleration data from the angular velocity data and recognizes the quiescence-pattern data in the angular acceleration data.

The memory 60 is communicatively coupled to the gyroscope 40 to receive the angular velocity data and to store the angular velocity data with a correlated time. In one implementation of this embodiment, the correlated time is the time at which the angular velocity data was output to the memory 60. In this case, the angular velocity data is time stamped on output to the memory 60. In another implementation of this embodiment, the memory 60 is communicatively coupled to the gyroscope 40 via the micro-controller 50. In this case, the micro-controller 50 generates the correlated time and outputs the sensed angular velocity data and the correlated time to the memory 60. In another implementation of this embodiment, the correlated time is the time at which the angular velocity data was received at the micro-controller 50 minus a known latency for the data to be sent from the gyroscope 40 to the micro-controller 50. In this case, the known latency is deleted from the time of receipt of the angular velocity data at the micro-controller 50.

In an implementation in which the micro-controller 50 generates angular acceleration data from the angular velocity data, the angular acceleration data is stored in the memory 60 with a time stamp.

The memory 60 is also communicatively coupled to the accelerometer 30 to receive the linear acceleration data and to store the linear acceleration data with the correlated time. In one implementation of this embodiment, the correlated time is the time at which the linear acceleration data was output to the memory 60. In another implementation of this embodiment, the memory 60 is communicatively coupled to the accelerometer 30 via the micro-controller 50. The correlated time for the linear acceleration data is generated as described above for the angular velocity data.

In one implementation of this embodiment, the micro-controller 50 is clocked with a crystal oscillator and is programmable with the current date and time. In this manner, the elapsed time is measured and each sensed acceleration/velocity data received at the micro-controller 50 is time stamped with the date and time of the receipt of the message.

The communication link between the memory 60 and the gyroscope 40 and/or the accelerometer 30 comprises one or more of a wireless communication link (for example, a radio-frequency (RF) communication link) and/or a wired communication link (for example, an optical fiber or copper wire communication link). The communication link between the micro-controller 50 and the gyroscope 40 and/or the accelerometer 30 comprises one or more of a wireless communication link (for example, a radio-frequency (RF) communication link) and/or a wired communication link (for example, an optical fiber or copper wire communication link). The communication link between the memory 60 and the micro-controller 50 comprises one or more of a wireless communication link (for example, a radio-frequency (RF) communication link) and/or a wired communication link (for example, an optical fiber or copper wire communication link).

In one implementation of this embodiment, the memory 60 stores both angular velocity for three directions and linear acceleration for three directions for the same correlated time. In one implementation of this embodiment, the linear acceleration, the angular velocity and the correlated time are stored in a table that sorts the table to store the accelerations in the sequence in which they were sensed. An exemplary table is shown as Table 1.

TABLE 1

Angular velocity and linear acceleration at correlated times.

| Correlated time | Angular Velocity (X) Degrees/s | Angular Velocity (Y) Degrees/s | Angular Velocity (Z) Degrees/s | Linear Accel. (X) m/s$^2$ | Linear Accel. (Y) m/s$^2$ | Linear Accel. (Z) m/s$^2$ |
|---|---|---|---|---|---|---|
| $t_1$ | 6 | 0 | 0 | 0 | 0 | 0 |
| $t_2$ | 0 | 0 | 0 | 0 | 0 | 0 |
| $t_3$ | 0 | 0 | 0 | 0 | 0 | 0 |
| $t_4$ | 0 | 0 | 0 | 0 | 0 | 0 |
| $t_5$ | 0 | 0 | 0 | 0 | 0 | 0 |

The micro-controller 50 includes one or more processors 52 that execute software 55 that is stored in a storage medium 56. The software 55 is executed by the processor 52 to determine if sensed angular velocity data and/or linear acceleration data matches quiescence-pattern data. The software 55 executed by processor 52 is implemented to determine if the angular velocity data follows the quiescence-pattern data for at least two consecutive times such as $t_2$ and $t_3$ or $t_2$, $t_3$, $t_4$ and $t_5$ (Table 1).

The stillness-event signal is generated by the micro-controller 50 if the linear acceleration data and the angular velocity data follow the quiescence-pattern data. In an implementation in which the sensor unit 10 does not include an accelerometer, a stillness-event signal is generated by the micro-controller 50 when the angular velocity data follows the quiescence-pattern data. In an implementation in which the sensor unit 10 does not include a gyroscope, the stillness-event signal is generated by the micro-controller 50 if the linear acceleration data follows the quiescence-pattern data.

The stillness-event signal is wirelessly transmitted from a radio frequency transmitter 70 via the antenna 80. The radio frequency transceiver 70 is communicatively coupled to the micro-controller 50 and the antenna 80. The micro-controller 50 communicates with the radio frequency transceiver 70 via a wireless communication link (for example, a radio-frequency (RF) communication link) or a wired communication link (for example, an optical fiber or copper wire communication link).

The kinematics of a sleeping human body as known in the art are used to generate the software 55 based on the position of each accelerometer 30 to ensure that the quiescence-pattern data is actually of an unconscious monitored person and not a sleeping monitored person. For example, during sleep the monitored person may move their feet or hands slightly without moving the torso. In addition, during sleep the monitored person may roll over at least one time per two hours. Thus, in one implementation of this embodiment, the monitored person locates a plurality of accelerometers 30, one on each hand and foot before going to sleep so the sensor unit 10 can sense the linear acceleration due to the small hand and/or foot movements during sleep. In another implementation of this embodiment, the monitored person locates an accelerometer 30, on each hand and each foot and a gyroscope 40 on their shoulder before going to sleep so the accelerometers 30 sense the linear acceleration due to the small hand and/or foot movements during sleep and the gyroscope 40 senses the angular velocity when they roll over.

Likewise the kinematics of a human body slumping forward into a state of unconsciousness while sitting down are known in the art and the pattern of the slumping can be used to generate the software 55. If the quiescence-pattern data is preceded by a slumping pattern, the sensor unit 10 has additional data to confirm the onset of the stillness event.

The sensor unit 10 is powered by a battery 65. The battery can be a fuel cell, a primary or non-rechargeable battery, a secondary or rechargeable battery, a thin-film battery, and the like.

Figure 2:
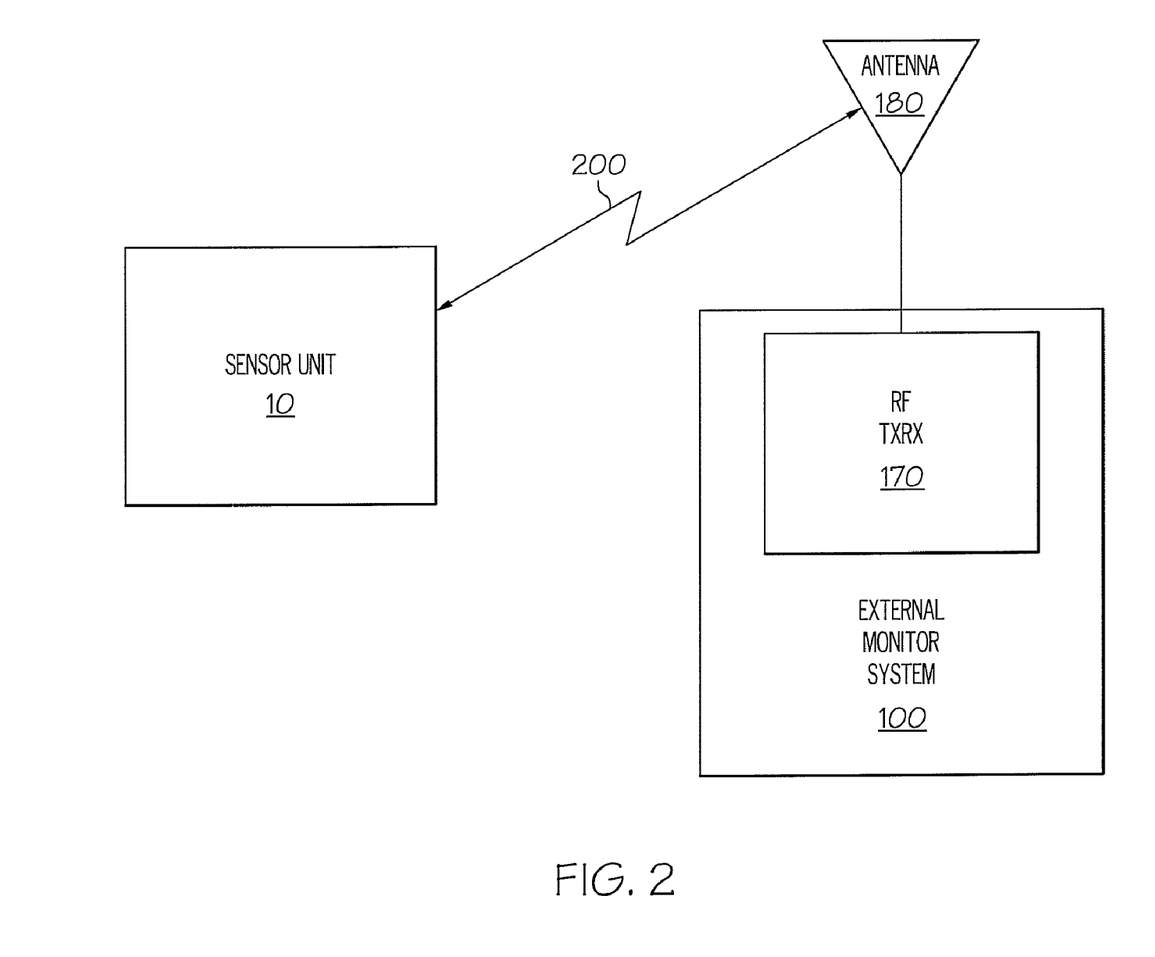
FIG. 2 is a block diagram of one embodiment of a sensor unit to detect a stillness event in communication with an external monitor system in accordance with the present invention.

FIG. 2 is a block diagram of one embodiment of a sensor unit 10 to detect a stillness event in communication with an external monitor system 100 in accordance with the present invention. The antenna 180 receives wireless signals from the sensor unit 10 via wireless communication link 200. The antenna 180 is communicatively coupled to the radio frequency transceiver (RF TXRX) 170, which receives the signals and transmits them for review to a monitor in the external monitor system 100. In another implementation of this embodiment, the communication link 200 is partially wireless and partially wired. In yet another implementation of this embodiment, an antenna in a home-based wireless device (for example, a wireless laptop) in the home of the monitored person receives the wireless signals transmitted from antenna 80 in the sensor unit 10. Then the home-based device connects to the external monitor system 100 via communication links (either wireless or wired) to send the stillness-event signal to the external monitor system 100. In one implementation of this embodiment, the device is a personal computer and the stillness-event signal received at the personal computer is transmitted via the Internet to the external monitor system 100. In another implementation of this embodiment, the software to analyze the angular velocity data and the memory are located in the external monitor system 100. In this implementation, the angular velocity data is analyzed by one or more processors at the external monitor system 100 and the stillness-event signal is generated at the external monitor system 100. In yet another implementation of this embodiment, the external monitoring system 100 includes a processor that is clocked with a crystal oscillator and is programmable with the current date and time. In this manner, the elapsed time is measured and each sensed acceleration/velocity data received at the monitoring system 100 is time stamped with the date and time of the receipt of the message.

In yet another implementation of this embodiment, at least one processor 52 and the external monitor system 100 are both clocked with crystal oscillators that are programmable with the current date and time. This allows the elapsed time to be measured at the micro-controller 50 and the external monitor system 100. In this implementation the sensed acceleration/velocity data received at both the micro-controller 50 and the external monitor system 100 is time stamped with the date and time of the receipt of the message.

The quiescence-patter data includes zero-value linear acceleration data for a duration greater than a selected duration, zero-value angular velocity data for a duration greater than a selected duration, zero-value linear acceleration data and zero-value angular velocity data for a duration greater than a selected duration, zero-value angular acceleration data for a duration greater than a selected duration, and zero-value linear acceleration data and zero-value angular acceleration data for a duration greater than a selected duration. In one implementation of this embodiment, the quiescence-pattern data also includes zero-value linear acceleration data and zero-value angular velocity data for a duration greater than a selected duration that follow an angular velocity about one-axis. The quiescence-pattern data also includes zero-value linear acceleration data and zero-value angular velocity data for a duration greater than a selected duration that follow an angular velocity about two-axes. In one implementation of this embodiment, the selected duration is selected based on input regarding the individual wearing the sensor unit 10. If an individual is known to frequently move while sleeping, the selected duration is shorter than for an individual known to lie relatively still while sleeping.

In the exemplary Table 1, a sensed angular velocity about the X-direction at time $t_1$ is followed by a period of zero-value linear acceleration data and zero-value angular velocity data in all three directions (X, Y, and Z). In Table 1, the linear acceleration data and angular velocity data is zero-value in all three directions for the duration of time from $t_2$ to $t_5$. In one implementation of this embodiment, the linear acceleration data and angular velocity data is zero-value in all three directions for the duration of time from $t_2$ to $t_N$ where $(t_N-t_2)$ is greater than the selected duration. In this case, the stillness-event signal is transmitted to the external monitor system 100 and a message, such as the exemplary message, "Joe Smith has not moved from 2:36 PM to 6:36 PM on Saturday, Jun. 10, 2006" is displayed on a monitor (not shown) at the external monitor system 100. In another implementation of this embodiment, the stillness-event signal is transmitted to the external monitor system 100 and an audio message, such as the exemplary message, "Joe Smith located at 10 Elm Street in Ocean View, Calif. has not moved from 2:36 PM to 6:36 PM on Saturday, Jun. 10, 2006" is delivered to a person on a telephone located at the external monitor system 100. In this latter implementation, the address may be generated by a global positioning system in the sensor unit 10. Alternatively in this latter implementation, the address may be generated by information in the memory 60 in the sensor unit 10 that the monitored person is housebound at 10 Elm Street in Ocean View, Calif.

In an exemplary implementation of this embodiment, the monitored person is a soldier, who is being monitored while in combat. If the angular velocity data and the linear acceleration data indicate that the soldier fell in a falling-event as described in the H0012340-5822 application and if the fall is followed by a stillness-event, the external monitor system receives a stillness-event signal to indicate the soldier is immobile. This can indicate a soldier is wounded or dead and the response to a stillness-event signal is to attempt to get assistance to the soldier. In the case of a monitored person as a fallen soldier, the time duration before a stillness event is determined is smaller than the time duration before a stillness event is determined for a sleeping person.

Figure 3:
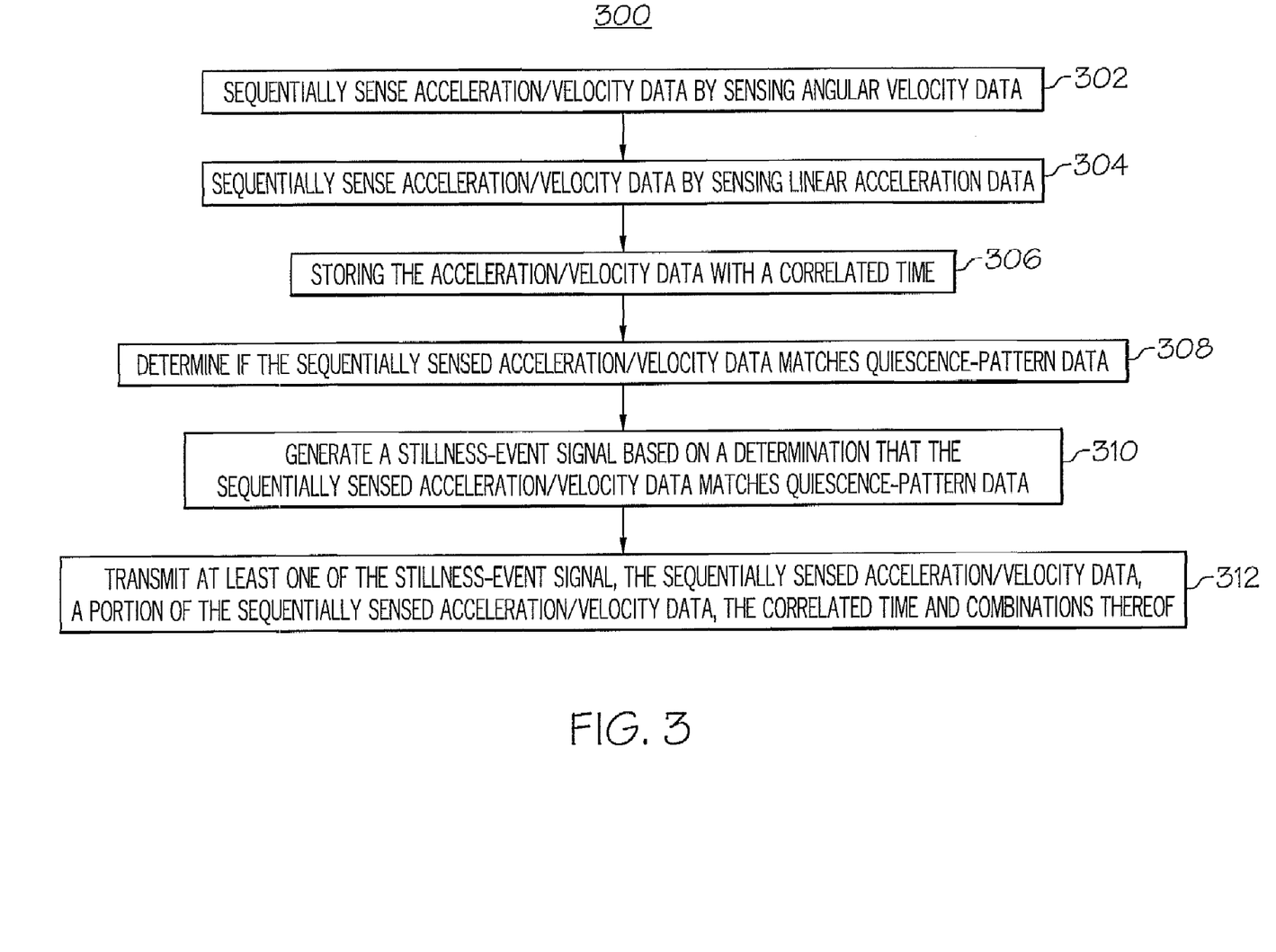
FIG. 3 is a flow diagram of one embodiment of a method to sense a stillness event in accordance with the present invention.
Figure 4A:
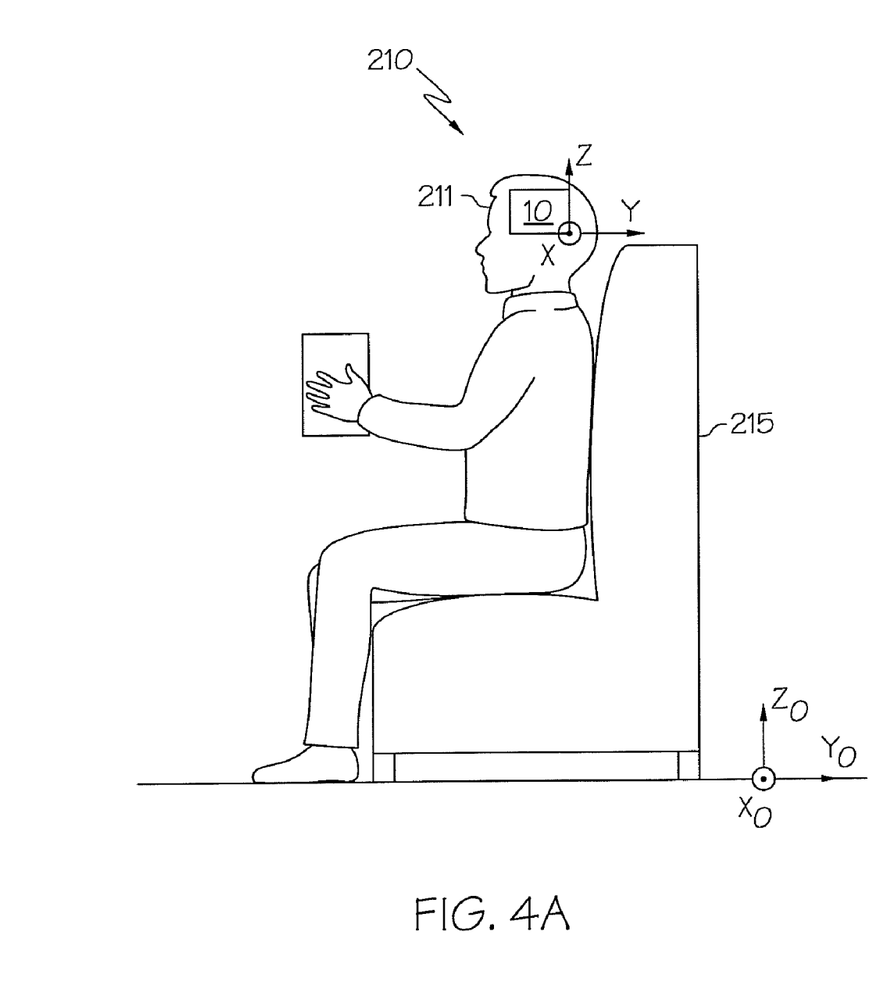
FIGS. 4A and 4B show diagrams of a monitored person before and after a stillness event in which a sensor unit is implemented in accordance with the present invention.
Figure 4B:
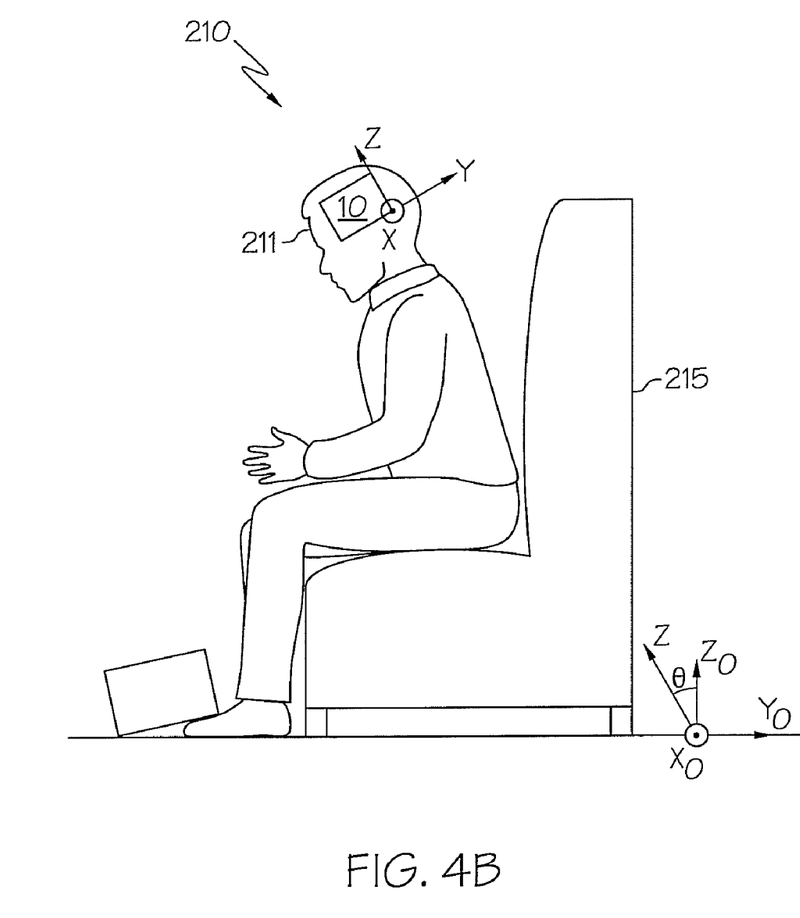

FIG. 3 is a flow diagram of one embodiment of a method 300 to sense a stillness event in accordance with the present invention. Method 300 is described with reference to sensor unit 10 and with reference to an exemplary stillness event as depicted in FIGS. 4A and 4B. FIGS. 4A and 4B show diagrams of a monitored person before and after a stillness event in which a sensor unit is implemented in accordance with the present invention. The person, represented generally by the numeral 210, is also referred to here as "monitored person 210."

At block 302, the sensor unit sequentially senses acceleration/velocity data by sensing angular velocity data at a gyroscope attached to the monitored person. In one implementation of this embodiment, the MEMS gyroscope 40 in the sensor unit 10 that is attached to the monitored person 210 sequentially senses acceleration/velocity data by sensing angular velocity data. In another implementation of this embodiment, sequentially sensing angular velocity data includes calculating angular acceleration data by differentiating the angular velocity data. In this case, the acceleration/velocity data includes the angular acceleration data. In one embodiment of this implementation, the micro-controller 50 differentiates the angular velocity data to generate the angular acceleration data.

At block 304, the sensor unit sequentially senses acceleration/velocity data by sensing linear acceleration data at the accelerometer attached to the monitored person. In one implementation of this embodiment, the MEMS accelerometer 30 in the sensor unit 10 that is attached to the monitored person 210 sequentially senses acceleration/velocity data by sensing linear acceleration data.

As shown in sequential time frames in FIGS. 4A and 4B, monitored person 210 falls into an unconscious state. At the time $t_o$ depicted in FIG. 4A, the monitored person 210 is sitting in a chair 215 with their head 211 upright in the Z-direction parallel to the Z axes of the sensor unit 10, which is attached to the head 211 of the monitored person 210. Just prior to the exemplary stillness event, the sensor unit 10 is located at a position at the origin of the X, Y, and Z axes. The X, Y, and Z axes are parallel to the $X_o$, $Y_o$, and $Z_o$ axes, respectively, which form a basis for the local environment and which are shown near the chair 215.

At a time $t_1$ depicted in FIG. 4B, the head 211 of the monitored person 210 has moved down and slightly forward and the Z axis of the sensor unit 10 is at an angle θ angle with respect to the $Z_o$ axis of the basis vectors ($X_o$, $Y_o$, and $Z_o$) shown near the chair 215. Thus, the position of the sensor unit 10 has rotated about the X-axis by an angle θ within the time $(t_1-t_0)$ so the sensor unit 10 experienced an angular velocity about the X-axis of $[\theta/(t_1-t_0)]$. As the head 211 of monitored person 210 falls forward in the moments preceding the stillness event, during the time frame from $t_0$ to $t_1$, the sensor unit 10 moves forward at a constant velocity for is a linear acceleration of zero (0) in the negative Y-direction and in the negative Z-direction. There is no linear acceleration of the sensor unit 10 in the X-direction. The numbers in the first row of Table 1 are indicative of the sensed angular velocity data during the time frame from $t_0$ to $t_1$.

After the time $t_1$ depicted in FIG. 4B, the head 211 of the monitored person 210 remains is at the angle θ through the times $t_2$, $t_3$, $t_4$ and $t_5$ (Table 1). If $(t_5-t_2)$ is greater than the selected duration, the monitored person 210 has experienced a stillness event between the times $t_1$ and time $t_5$. In one implementation of this embodiment, the head 211 of the monitored person 210 remains is at a θ angle between the Z axis of the sensor unit 10 and the $Z_o$ axis near the base of the chair 215 though the time $t_2$ to time $t_N$ where $(t_N-t_2)$ is equal to or greater than the selected duration. In this case, the monitored person 210 has experienced a stillness event between the times $t_1$ and $t_N$.

At block 306, the micro-controller stores the acceleration/velocity data with a correlated time. In one implementation of this embodiment, the micro-controller 50 stores the acceleration/velocity data with a correlated time, such as one of the times $t_1$, $t_2$, $t_3$, $t_4$ or $t_5$, in the memory 60 of sensor unit 10. In another implementation of this embodiment, the micro-controller 50 stores the acceleration/velocity data with a correlated time in a table, such as Table 1, in the memory 60 of sensor unit 10. In yet another implementation of this embodiment, the micro-controller 50 transmits the acceleration/velocity data with a correlated time for storage in the external monitor system 100 via the transceiver 70, antenna 80 and communication link 200.

At block 308, the micro-controller determines if the sequentially sensed acceleration/velocity data matches quiescence-pattern data. In one implementation of this embodiment, the micro-controller 50 determines if the sequentially sensed acceleration/velocity data, including the angular velocity data and linear acceleration data sensed during blocks 302 and 304, respectively, matches quiescence-pattern data as defined above with reference to FIG. 2.

At block 310, the micro-controller generates a stillness-event signal based on a determination that the sequentially sensed acceleration/velocity data matches quiescence-pattern data. In one implementation of this embodiment, the micro-controller 50 generates the stillness-event signal based on sequentially sensed acceleration/velocity data that matches the quiescence-pattern data in Table 1.

At block 312, the micro-controller transmits at least one of the stillness-event signal, the sequentially sensed acceleration/velocity data, a portion of the sequentially sensed acceleration/velocity data, the correlated time, and combinations thereof. In one implementation of this embodiment, micro-controller 50 transmits the stillness-event signal to the external monitor system 100 when the micro-controller 50 determines the sequentially sensed acceleration/velocity data that matches the quiescence-pattern data. In another implementation of this embodiment, the micro-controller 50 transmits the sequentially sensed acceleration/velocity data and the correlated times to the external monitor system 100 and processors (not shown) in the external monitor system 100 determine that the sequentially sensed acceleration/velocity data matches a quiescence-pattern data and generate a stillness-event signal. In yet another implementation of this embodiment, the accelerometer 30 and the gyroscope 40 send the sensed acceleration/velocity data to the micro-controller 50 and the micro-controller 50 sends the unprocessed sensed acceleration/velocity data to the external monitor system 100 via communication link 200. In this case, processors in the external monitor system 100 store the acceleration/velocity data with a correlated time, determine if the sequentially sensed acceleration/velocity data matches a quiescence-pattern data and generates a stillness-event signal.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A sensor unit to detect a stillness event, the sensor unit comprising:
   a gyroscope attached to a monitored person, the gyroscope adapted to sense an angular velocity of the monitored person and to output angular velocity data based on the sensed angular velocity;
   a micro-controller communicatively coupled to the gyroscope, the micro-controller adapted to receive the angular velocity data, to recognize a quiescence-pattern data in the angular velocity data, and to generate a stillness-event signal upon recognition of the quiescence-pattern data for a duration greater than a selected duration; and
   a memory communicatively coupled to receive and to store the angular velocity data with a correlated time.

2. The sensor unit of claim 1, the sensor unit further comprising:
   an accelerometer attached to the monitored person, the accelerometer adapted to sense a linear acceleration of the monitored person and to output linear acceleration data based on the sensed linear acceleration, wherein the micro-controller is communicatively coupled to the accelerometer to receive the linear acceleration data and to recognize the quiescence-pattern data in the angular velocity data and linear acceleration data, and wherein the memory is communicatively coupled to the accelerometer to receive and to store the linear acceleration data with a correlated time.

3. The sensor unit of claim 2, wherein the quiescence-pattern data comprises zero-value linear acceleration data, zero-value angular velocity data, zero-value linear acceleration data and zero-value angular velocity data, zero-value angular acceleration data, and zero-value linear acceleration data and zero-value angular acceleration data.

4. The sensor unit of claim 1, the sensor unit further comprising:
   a radio frequency transmitter; and
   an antenna communicatively coupled to the radio frequency transmitter, wherein the antenna further communicatively coupled to an external monitor system.

5. The sensor unit of claim 1, wherein the quiescence-pattern data includes zero-value linear acceleration data and zero-value angular acceleration data, calculated from the angular velocity data.

6. The sensor unit of claim 5, the sensor unit further comprising:
   a radio frequency transmitter; and
   an antenna communicatively coupled to the radio frequency transmitter, the antenna further communicatively coupled to an external monitor system.

7. A method to sense a stillness event, the method comprising:
   sequentially sensing acceleration/velocity data;
   storing the acceleration/velocity data with a correlated time; and
   determining if the sequentially sensed acceleration/velocity data matches quiescence-pattern data for a duration greater than a selected duration.

8. The method of claim 7, the method further comprising:
   generating a stillness-event signal based on a determination that the sequentially sensed acceleration/velocity data matches quiescence-pattern data.

9. The method of claim 8 the method further comprising:
   transmitting the stillness-event signal.

10. The method of claim 7, wherein sequentially sensing acceleration/velocity data comprises:
    sensing angular velocity data.

11. The method of claim 10, wherein sequentially sensing acceleration/velocity data further comprises:
    sensing linear acceleration data.

12. The method of claim 7, wherein sequentially sensing acceleration/velocity data comprises:
    sensing linear acceleration data.

13. A program product comprising program instructions, embodied on a storage medium, that are operable to cause a programmable processor to:
    sequentially sense acceleration/velocity data;
    store the acceleration/velocity data with a correlated time; and
    determine if the sequentially sensed acceleration/velocity data matches quiescence-pattern data, wherein the quiescence-pattern data includes sensing zero-value linear acceleration data for a duration greater than a selected duration and recognizing zero-value angular acceleration data, calculated from an angular velocity data sensed for a duration greater than a selected duration.

14. The program product of claim 13, further comprising instructions operable to cause the programmable processor to:
    generate a stillness-event signal based on a determination that the sequentially sensed acceleration/velocity data matches the quiescence-pattern data.

15. The program product of claim 14, further comprising instructions operable to cause the programmable processor to:
    transmit the stillness-event signal based on a generation of the stillness-event signal.

16. The program product of claim 13, wherein instructions operable to cause the programmable processor to sequentially sense acceleration/velocity data comprises instructions operable to cause the programmable processor to:
    sense angular velocity data.

17. The program product of claim 16, wherein instructions operable to cause the programmable processor to sequentially sense acceleration/velocity data comprises instructions operable to cause the programmable processor to:
    sense linear acceleration data.

* * * * *